United States Patent [19]

Figurski

[11] Patent Number: 5,784,435
[45] Date of Patent: Jul. 21, 1998

[54] X-RAY TUBE SUPPORT COLUMN ON A MOBILE X-RAY PRODUCT WITH IMPROVED ROTATIONAL FLEXIBILITY

[75] Inventor: Mark A. Figurski, Hartland, Wis.

[73] Assignee: General Electric Company, Milwaukee, Wis.

[21] Appl. No.: 839,085

[22] Filed: Apr. 23, 1997

[51] Int. Cl.$^6$ .................................................. H05G 1/02
[52] U.S. Cl. .................................................. 378/197; 378/198
[58] Field of Search .................................. 378/197, 198, 378/193, 196

[56] References Cited

U.S. PATENT DOCUMENTS

| | | | |
|---|---|---|---|
| 4,335,315 | 6/1982 | Waerve et al. | 378/197 |
| 4,752,948 | 6/1988 | MacMahon | 378/198 |
| 5,351,282 | 9/1994 | Kadowski et al. | 378/197 X |
| 5,499,284 | 3/1996 | Pellegrino et al. | 378/198 |
| 5,506,883 | 4/1996 | Exner | 378/197 X |

Primary Examiner—David P. Porta
Attorney, Agent, or Firm—Barbara J. Haushalter; John H. Pilarski

[57] ABSTRACT

An x-ray unit is provided which includes an x-ray device for producing x-rays. A base holds the x-ray device, which comprises an x-ray source for positioning over an area of concern, and a rotatable x-ray source support column for allowing movement of the x-ray source. The total rotational motion of the support column is greater than 360° relative to the base. Mechanical end of rotation stops mechanically defining total rotational motion of the support column. The x-ray source is capable of clockwise and counterclockwise movement from a parked position.

9 Claims, 3 Drawing Sheets

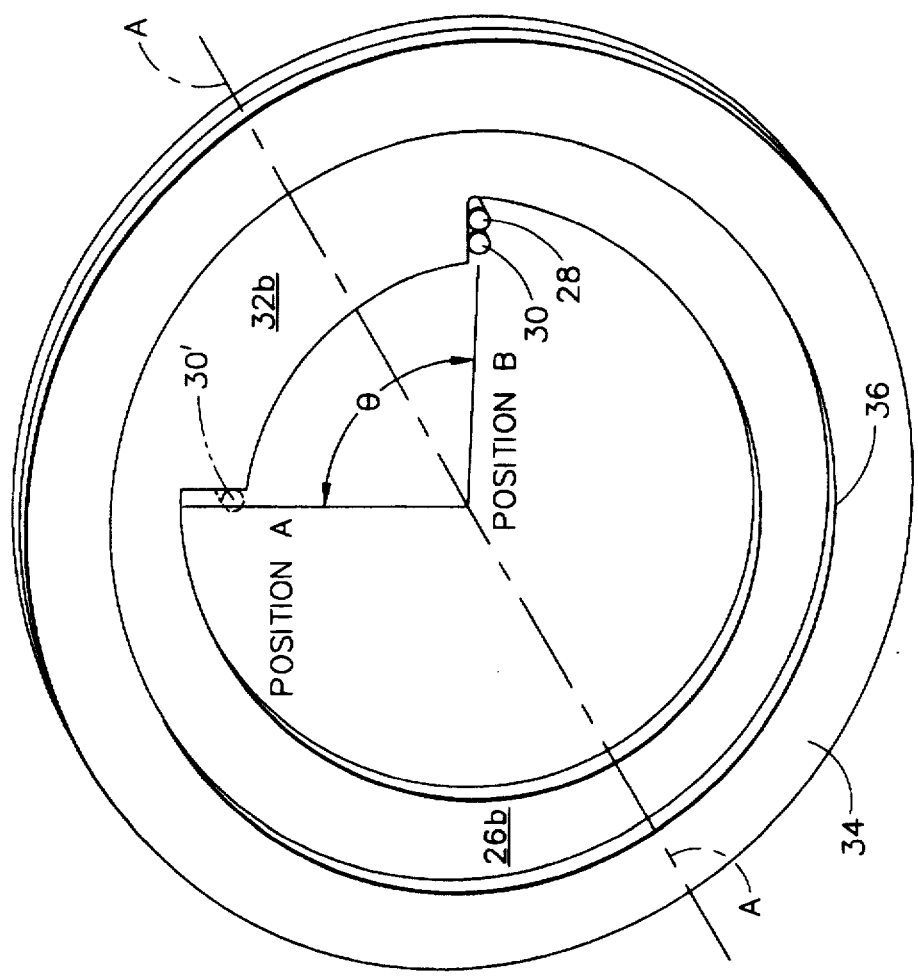
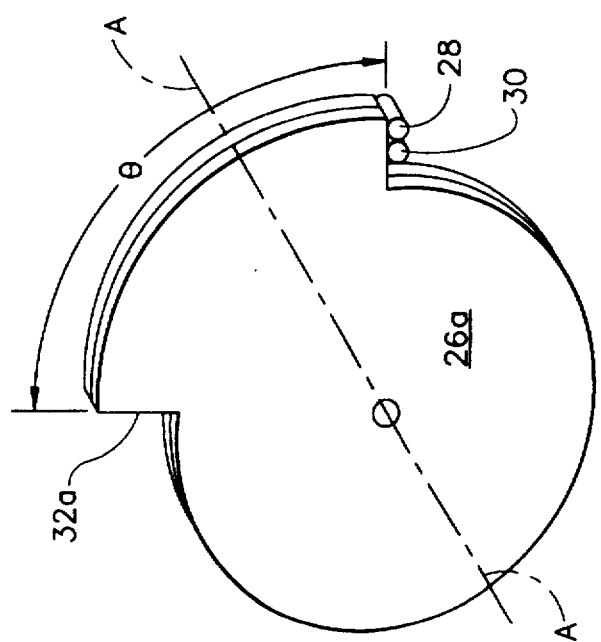
FIG. 3B
FIG. 3A 3,784,435

1

X-RAY TUBE SUPPORT COLUMN ON A MOBILE X-RAY PRODUCT WITH IMPROVED ROTATIONAL FLEXIBILITY

TECHNICAL FIELD

The present invention relates to x-ray tubes and, more particularly, to improved rotational flexibility of a positioning device used for the source or receiver in a medical device.

BACKGROUND ART

Mobile x-ray equipment is a necessity in many environments, such as medical, so that it can be moved to various locations. Mobile x-ray equipment is moved from patient-to-patient throughout hospitals such as, for example, in emergency, intensive care, pediatrics and surgery. In many types of x-ray equipment, it is also necessary to provide an x-ray source which can be readily moved over the patient. This is especially true for mobile x-ray products in which the x-ray machine is transported to the patient's room or location and with which an x-ray exposure is taken of the area of concern.

An x-ray source is typically mounted on a support column. Current column tube supports are generally limited to a total rotational value of 3600 or less, to allow the use of mechanical end of travel stops and to prevent entanglement of high voltage cables used to provide electrical power to the x-ray tube. Unfortunately, providing a total column rotational motion of 360° typically results in a rotational motion of 0° of travel in one direction and 360° of travel in the other direction. This, consequently, forces repositioning of the mobile unit or tube support if parked on the side of the bed opposite that which the tube support is parked. However, if rotation greater than 360° is used, electromechanical devices are typically incorporated. Unfortunately, such devices consume part of an already limited electrical supply (e.g., battery power) or require the unit to be plugged into a wall receptacle prior to use of the machine. This, in turn, provides additional limits to the mobile x-ray unit range or areas in which it can be used.

It would be desirable then to have an x-ray support column which could allow for rotational motion total greater than 360° which is limited by a mechanical device, which allows an operator of the x-ray device to move the unit in either direction without restriction, subsequently eliminating the need to reposition the equipment, column, or requirement to park the unit on a specific side of the patient bed.

SUMMARY OF THE INVENTION

The present invention increases finite rotational motion of an x-ray tube support column on a mobile x-ray product from 0° to any angle up to, for example, 720°. The device of the present invention is purely mechanical, so as not to tax the limited electrical supply of the mobile x-ray unit. The device allows an operator to remove the x-ray tube from a park position and rotate it in either direction so as to position the x-ray source over the patient without having to take into consideration which side of the patient the portable x-ray machine is on.

In accordance with one aspect of the present invention, an x-ray device having an associated platform base for holding the device comprises an x-ray source for positioning over an area of concern. A rotatable x-ray tube support column allows movement of the x-ray source, wherein the total rotational motion of the support column is greater than 360° relative to the base.

2

Accordingly, it is an object of the present invention to provide a mechanical device which allows rotational travel greater than 360° of the column relative to the base. It is a further object of the present invention that it utilizes a mechanical stop without electrical feedback. Finally, it is an object of the present invention to provide a device wherein an operator can remove the x-ray tube from a park position and rotate it in either direction to position the x-ray source over the patient without having to take into consideration which side of the patient the portable x-ray machine is on.

Other objects and advantages of the invention will be apparent from the following description, the accompanying drawings and the appended claims.

BRIEF DESCRIPTION OF THE DRAWINGS

FIGS. 3A and 3B are isometric views illustrating the operational configuration for achieving the rotational flexibility of the present invention.

DETAILED DESCRIPTION OF THE PREFERRED EMBODIMENTS

The present invention provides an x-ray device wherein the tube is mounted on a support column that is rotatable in either position from a park position, with a total rotational travel greater than 360°.

Figure 1:
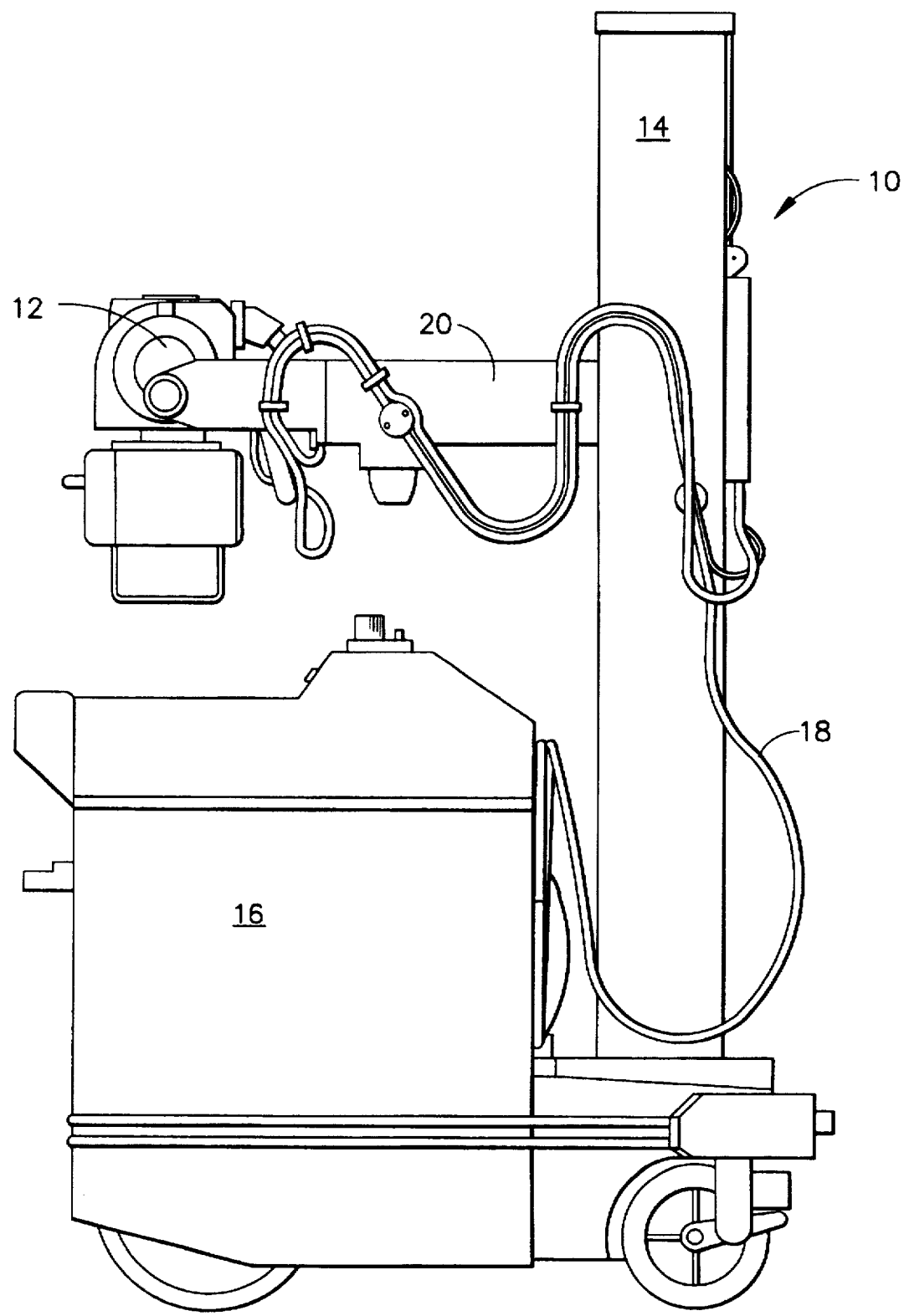
FIG. 1 is a prior art side view of a mobile x-ray device, illustrating mounting of the x-ray source.

Referring now to FIG. 1, there is illustrated a side view of a typical mobile x-ray unit 10. An x-ray source 12, mounted to the end of a horizontal arm 20, is positionable over an area of concern on a patient. The x-ray source 12 is typically mounted through a gimbal type arrangement in which the column 14 is required to rotate to move the x-ray source from the park position on the mobile x-ray unit base 16 to the appropriate position in order to take an x-ray exposure of the patient.

The rotational movement of the column 14 is typically limited to a value of 360° or less, to allow the use of mechanical end travel stops and to prevent entanglement of high voltage cables 18 used to provide electrical power to the x-ray tube 12. In prior art systems, this provides a total column rotational motion of 360°, with a rotational motion of 0° of travel in one direction and 360° of travel in the opposite direction.

Figure 2A:
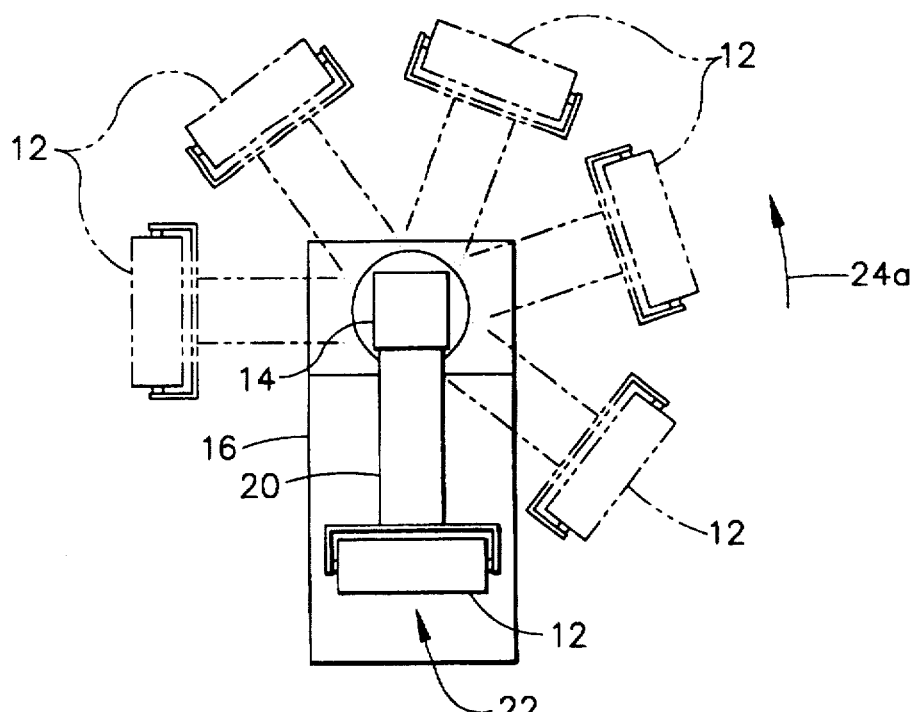
FIGS. 2A and 2B are top views of a mobile x-ray device illustrating the rotational flexibility achieved with the present invention.
Figure 2B:
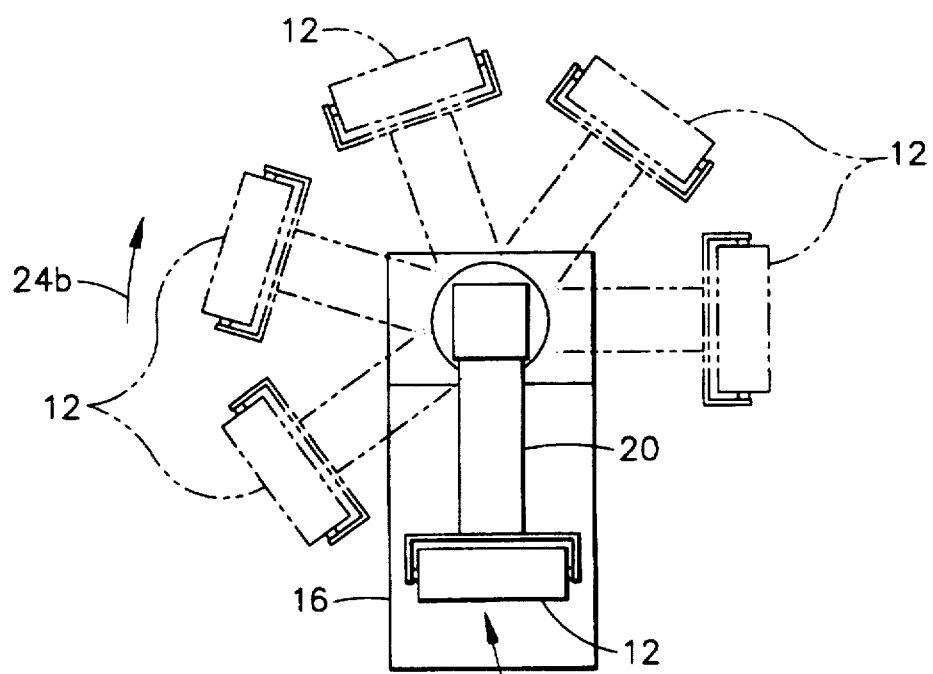

Referring now to FIGS. 2A and 2B, there is illustrated the feature of the present invention wherein rotational movement of the tube 12 is allowed in either direction from a park position. The present invention is capable of a rotational movement of at least 270° in either direction, and preferably somewhat greater than 270° to allow for an added margin of operation, with a total rotational travel of at least 5400°. The park position is illustrated in FIGS. 2A and 2B by solid lines, as position 22, with zero degrees of rotation. As illustrated by the dotted line indications of source 12, the operator of the x-ray unit 10 is allowed to move the unit 10 in either direction, indicated by arrow 24a (counterclockwise) in FIG. 2A, and arrow 24b (clockwise) in FIG. 2B. This has the advantage of eliminating the need to reposition the equipment or column. This also eliminates the requirement to park the unit 10 on a specific side of the patient.

Operationally, the device of the present invention requires two reference points. The first reference point is typically a fixed reference point relative to rotation and may be contained, for example, on the base 16. The second reference point can be a rotational reference point, and can be associated with the rotational movement of any rotating element of the unit 10. For example, the rotational reference point may be contained within the column 14 used for rotational motion of the gimbal type arrangement of FIG. 1, supporting the x-ray source 12.

Referring now to FIGS. 3A and 33, there is illustrated isometric views of the operational configuration of the present invention. A rotation plate 26 is located between fixed reference point 28 and rotational reference point 30. Configuration of the rotation plate 26 as well as placement of the fixed and rotational reference points 28 and 30, respectively, is determined by the device to which the mechanism of the present invention is to be applied. The rotational reference point 30 rotates relative to the fixed reference point 28 about a defined axis of rotation A—A. The rotation plate 26 is preferably fabricated in a generally circular manner, with an external protrusion 32a provided outside the circular path as illustrated in FIG. 3A, or an internal protrusion 32b provided inside the circular path as illustrated in FIG. 3B, depending upon where the rotation constraint is placed on the rotation plate 26. The rotation constraint is that bearing surface which constrains or determines the relative rotational motion of the rotation plate about axis A—A. In FIG. 3A, the rotation constraint may be, for example, a ball bearing or pin located at axis A—A, whereas in FIG. 3B, wall 36 between rotation plate guide 34 and rotation plate 26 provides the bearing surface constraining the rotation.

Continuing with FIGS. 3A and 3B, the angular size of the protrusion 32 as well as the physical size of the reference point 28 and 30 objects (e.g., pin, boss, stop, or other suitable equivalent) dictate the total rotational motion allowed between the fixed reference point 28 and the rotational reference point 30. As the relative travel of the rotation plate 26 between the rotational and fixed reference points (prior to the points acting as end of travel stops) is one half that of the angular rotational travel, the following formula can be used to calculate the total amount of rotational motion:

$$\phi = 2(360 - \theta)$$

where ⌀ is the total angular rotation (in degrees) of the relative reference point 30 to the fixed reference point 28, and e is the angular dimension (in degrees) measured between the centerlines of the rotational reference point 30 and the fixed reference point 28 when the reference plate protrusion 32 is placed in contact between the two points.

The rotational reference point 30 rotates, to rotated position rotational reference point 30' as shown in FIG. 3B, and provides the force necessary to move the rotation plate 26 until the protrusion 32 on the rotation plate provides a physical barrier between the relative and fixed reference points. When the rotational reference point 30 changes angular direction, it will traverse approximately 50% of the maximum angular displacement prior to contacting the rotation plate 26. At that point, the rotational reference point 30' will move the rotation plate 26 in the opposite direction until a physical stop is again encountered when striking the fixed reference point 28.

The invention has been described in detail with particular reference to certain preferred embodiments thereof, but it will be understood that modifications and variations can be effected within the spirit and scope of the invention.

I claim:

1. An x-ray unit comprising:

an x-ray device for producing x-rays;

a base for holding the x-ray device;

an x-ray source for positioning over an area of concern;

a rotatable x-ray source support column for allowing movement of the x-ray source, wherein the total rotational motion of the support column is greater than 360° relative to the base; and mechanical end of rotation stop means for mechanically defining total rotational motion of the support column.

2. An x-ray unit as claimed in claim 1 wherein the x-ray source is capable of clockwise and counterclockwise movement from a parked position.

3. An x-ray unit as claimed in claim 2 wherein the parked position locates the x-ray source between the support column and an operator of the apparatus.

4. An x-ray unit as claimed in claim 2 wherein total rotational movement of the x-ray source is greater than 540°.

5. An x-ray unit as claimed in claim 1 further comprising an arm, a first end of the arm attached in a substantially perpendicular relationship with the support column and a second end of the arm for supporting the x-ray source.

6. An x-ray unit as claimed in claim 1 further comprising a fixed reference point and a rotational reference point, with the rotational reference point rotating relative to the fixed reference point about a defined axis of rotation.

7. An x-ray unit as claimed in claim 6 further comprising a rotation plate located between the fixed reference point and the rotational reference point.

8. An x-ray unit as claimed in claim 7 wherein the rotation plate is fabricated in a generally circular manner, with an external protrusion provided outside a circular path or an internal protrusion provided inside the circular path.

9. An x-ray unit as claimed in claim 8 wherein an angular size of the protrusion as well as a physical size of the fixed and rotational reference points dictate total rotational motion allowed between the fixed reference point and the rotational reference point.

* * * * *